(12) United States Patent
Hornig et al.

(10) Patent No.: US 9,149,574 B2
(45) Date of Patent: Oct. 6, 2015

(54) PORT NEEDLE HAVING NEEDLE-PRICK PROTECTION DEVICE

(75) Inventors: Wolfgang Hornig, Kierspe-Bollwerk (DE); Marcel Oster, Mönchengladbach (DE); Jürgen Maurer, Friedrichsdorf (DE); Martina Papiorek, Hünfelden (DE); Bernhard Pech, Hünstetten (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 194 days.

(21) Appl. No.: 13/322,246

(22) PCT Filed: Jun. 7, 2010

(86) PCT No.: PCT/EP2010/057926
§ 371 (c)(1),
(2), (4) Date: Jan. 18, 2012

(87) PCT Pub. No.: WO2010/142641
PCT Pub. Date: Dec. 16, 2010

(65) Prior Publication Data
US 2012/0123344 A1    May 17, 2012

(30) Foreign Application Priority Data

Jun. 10, 2009  (DE) .......................... 10 2009 025 056
Feb. 16, 2010  (EP) ..................................... 10153708

(51) Int. Cl.
*A61M 5/00*    (2006.01)
*A61M 5/158*   (2006.01)

(52) U.S. Cl.
CPC ....... *A61M 5/158* (2013.01); *A61M 2005/1586* (2013.01)

(58) Field of Classification Search
USPC ........... 604/263, 115–117, 110, 93, 171, 192, 604/198, 289, 890, 310, 311, 195, 197, 187, 604/163, 264; 128/919; 206/363, 264, 365, 206/367, 438
See application file for complete search history.

(56) References Cited

U.S. PATENT DOCUMENTS

| | | | | |
|---|---|---|---|---|
| 3,073,306 | A * | 1/1963 | Linder | 604/198 |
| 4,725,267 | A * | 2/1988 | Vaillancourt | 604/192 |
| 4,897,083 | A * | 1/1990 | Martell | 604/192 |
| 5,304,136 | A * | 4/1994 | Erskine et al. | 604/110 |
| 5,336,199 | A * | 8/1994 | Castillo et al. | 604/198 |
| 5,772,636 | A * | 6/1998 | Brimhall et al. | 604/198 |
| 6,080,135 | A * | 6/2000 | Van Stokkum | 604/198 |

(Continued)

FOREIGN PATENT DOCUMENTS

| | | |
|---|---|---|
| WO | 02/055132 | 7/2002 |
| WO | 03/028784 | 4/2003 |
| WO | 2008/092958 | 8/2008 |

*Primary Examiner* — Scott Medway
(74) *Attorney, Agent, or Firm* — Occhiuti & Rohlicek LLP

(57) ABSTRACT

The present invention relates to a port needle comprising a bearing for resting and fixing the port needle on the patient, a feed, and a needle. This problem is solved according to the invention by a port needle comprising a bearing (1) for resting the port needle on the patient, a feed (6), and a needle (3) having a tip (21), it being possible to bring the needle (3) into at least two positions, a puncture position and a retracted position, characterized by a safety section (7), which shields the tip (21) of the needle (3) at least in the retracted position and thus forms a needle-prick protection device.

17 Claims, 13 Drawing Sheets

(56) References Cited

U.S. PATENT DOCUMENTS

| | | |
|---|---|---|
| 6,238,375 B1 | 5/2001 | Powell |
| 6,620,140 B1 * | 9/2003 | Metzger .................. 604/288.01 |
| 7,083,600 B2 * | 8/2006 | Meloul ........................ 604/263 |
| 7,147,624 B2 * | 12/2006 | Hirsiger et al. ............... 604/198 |
| 7,544,181 B2 * | 6/2009 | Axelsson et al. ............. 604/110 |
| 8,052,653 B2 * | 11/2011 | Gratwohl et al. ............. 604/198 |
| 8,545,455 B2 * | 10/2013 | Szucs ............................ 604/198 |
| 2002/0055711 A1 * | 5/2002 | Lavi et al. ..................... 604/110 |
| 2002/0072720 A1 * | 6/2002 | Hague et al. .................. 604/264 |
| 2003/0168366 A1 | 9/2003 | Hirsiger et al. |
| 2004/0199112 A1 | 10/2004 | Dalton |
| 2006/0015127 A1 * | 1/2006 | Chien ........................... 606/167 |
| 2006/0178626 A1 * | 8/2006 | Axelsson et al. ............. 604/110 |

\* cited by examiner

PORT NEEDLE HAVING NEEDLE-PRICK PROTECTION DEVICE

CROSS REFERENCE TO RELATED APPLICATIONS

This application is the national stage application of international application no. PCT/EP2010/057926, filed Jun. 7, 2010, which claims the priority of European application no. 10153708.2, filed Feb. 16, 2010, and German application no. 10 2009 025 056.5, filed on Jun. 10, 2009. The contents of these applications are incorporated herein by reference.

TECHNICAL FIELD

The present invention relates to a port needle having a bearing for resting the port needle on the patient, a feed line, and a needle with a tip.

Many such port needles are disclosed in the prior art and are used to establish a connection to a port implanted in the human or animal body. Such ports are implanted in order to permit simpler and more reliable introduction of substances into the human body, in particular into central vessels.

For the connection between port needle and port, a port needle has a needle with a needle tip. Such a needle tip is dangerous and is therefore generally enclosed by a needle guard in the state as supplied. This needle guard is removed shortly before application of the port needle. Although the needle is sterile at this point and does not pose a risk of infection, it nonetheless poses a risk of injury to the user.

By contrast, when the port needle is withdrawn from the patient or from the port within the patient, it is no longer sterile and thus not only poses a risk of injury but also a high risk of infection, not only to the medical personnel but also to the staff of the waste management business. For this reason, it is desirable to equip port needles with a needle-prick protection device, which in particular provides protection against needle-prick injuries during and after withdrawal of the port needle after use. This is also necessary in particular on account of increasing safety demands.

In the development of a needle-prick protection device, various aspects compete with one another. On the one hand, it is important that the grip area provided for the medical personnel when applying a needle is large and can be safely gripped, and that the safety mechanism is so robust that it is not triggered during the application. However, a high structure of the grip, together with complex safety technology, reduces the wearing comfort of the needle as far as the patient is concerned.

PRIOR ART

U.S. Pat. No. 6,238,375, for example, discloses a low structure of a needle-prick protection device, in which the needle is extracted from a narrow grip part, while at the same time two protection elements move apart from each other telescopically and thus hide the needle. In this approach, the narrow needle holder or the grip part is mounted on the upper telescope segment. The telescope segments are prevented from sliding through only in the direction of pulling, not in the outward direction. The needle protection is ensured by a dropping base plate, but the base plate is slotted in the middle for design reasons and therefore could not withstand a pressure from above.

WO03028784 discloses a stable and easily grippable design of a protected port needle, but the latter has a high structure with corners and edges and is therefore uncomfortable for the patient to wear, because the patient can easily bump the high structure against things or catch it on things, which can be painful and can also adversely affect the fit of the port needle.

DISCLOSURE OF THE INVENTION

A port needle according to the invention, in addition to having a bearing for resting the port needle on the patient, that is to say on the patient himself/herself or on the port implanted in the human or animal, a feed line, which can consist for example of a hose or of a connector for such a hose, and a needle with a tip, also has a safety section. The needle can be brought with its tip into at least two positions, namely a puncture position and a retracted position. In the puncture position, the needle protrudes far out with its tip. A port needle is generally supplied in such a puncture position, with the needle then surrounded by a needle guard. For use, the needle guard is removed. The port needle, located in the puncture position, can then be pushed directly into the port. In the retracted position, the needle tip is shielded according to the invention by the safety section.

This affords the advantage already mentioned in the introduction, whereby personnel are now protected against needle-prick injuries and infections. The safety section does not have to completely surround the needle, and instead it simply has to be designed such that, given reasonable handling, the needle tip is sufficiently shielded. This is even the case, for example, when the safety section is open at the bottom but the needle tip is recessed therein to such a degree that, upon contact with the human skin, the possibility of the tip of the needle touching the skin and in particular injuring the skin is ruled out. This is dependent not only on the depth by which the needle tip is concealed but also on the opening width of the safety section. Suitable dimensions can be readily worked out by a person skilled in the art.

The needle is preferably secured on a needle holder. The needle holder is preferably releasably connected by at least one connection, preferably a latching element, particularly preferably at least two latching elements or sliding or holding elements, to an element connected to the bearing or a device for locking the needle holder. The connection or latching is released by a pull exerted along the needle axis. The force needed to release the connection or latching can be influenced and determined, for example in the case of latching, by the latching angle of the latching elements, the width of the latching elements, the configuration of the geometrical pairing, and also the flexibility and the material combination.

For controlled application of the port needle, it is of great importance that the safety mechanism is not triggered too early, such that even in the event of a position correction, which in extreme cases can even mean removal from the port membrane and reinsertion, the port needle can be handled safely and in a controlled way. For this purpose, a latching mechanism can be provided, for example, which can be released by the release of a mechanism, for example a lever. It is preferable, however, if the safety mechanism is triggered by a pull exerted along the needle axis, in which case the force needed to trigger the safety mechanism is 5 N or more. It is particularly preferable if a force of at least 8 N is needed, preferably of ≥8 to ≤13 N, very particularly preferably of ≥9 to ≤11 N.

The releasable connection of the needle holder to the element connected to the bearing or to the device for locking the needle holder, which connection can be released by a force of 5 N or more, preferably of 8 N or more, particularly preferably of ≥8 to ≤13 N, very particularly preferably of ≥9 to ≤11

N, can also be achieved by means other than by latching, sliding or holding elements, for example by webs to be broken off, by adhesives or by plug connections.

To be able to act on the port needle with the force needed to trigger the safety mechanism, it is advantageous if the bearing of the port needle is wider than the device, connected to the bearing, for locking the needle holder. In this way, the bearing can be fixed by pressure, which facilitates the triggering of the safety mechanism and prevents the port needle from being removed from the port without the safety mechanism being triggered.

The bearing advantageously has a height compensation element, which is positioned between bearing and needle and is extensible and/or flexible.

Such a height compensation element is suitable not only for permitting small relative movements between bearing and needle, which movements occur when the patient moves, but also for compensating for height differences and variations between port base and bearing. Although port needles do exist that have needles of different lengths, by means of which it is possible to adapt the needle length to the individual installation situation of the port in the patient, such port needles can only be practically stocked in a discrete length variation of a few millimeters. In addition, the installation depth of the port may be subject to slight variations over the course of time or in the event of movement of the patient. Optimally, however, the needle reaches as far as the port base. It is thus possible, by means of a height compensation element, to ensure an optimal position of the needle tip and increase the wearing comfort.

It is not essential that the height compensation element is connected directly to the bearing and/or the needle. Instead, the connection can be provided by other elements. The important thing is simply that there is no stiff connection between bearing and needle. The height compensation element can consist, for example, of a flexible ring, in which case the height compensation can be ensured by an undulating configuration, or of an extensible spacer. Although compressible elements would also be suitable in principle to permit a relative movement between bearing and needle, such elements are suitable only to a very limited degree in that they also permit deeper insertion of the needle into the patient and can thus result in damage to the port or injuries to the patient. The height compensation element can, for example, be affixed, clamped on or injected on, or it can also be injected in a two-component technique.

The needle is preferably secured on a needle holder, in which the feed line is preferably also mounted. Such a needle holder protects the needle from breakage during handling and provides the personnel with good grip and a secure handle. Such a needle holder is advantageously mounted on an end of the needle, since the function as handle is then particularly clear. If the feed line is also integrated in the needle holder, a reliable and safe connection between feed line and needle can be achieved inside the needle holder.

It is particularly advantageous if first latching elements are provided, which latch the needle in the retracted position. Such first latching elements do not necessarily have to be mounted on the needle itself, and instead they can also be secured on other elements, for example on the needle holder. The latching is preferably irreversible or can be released only by applying a pressure of at least 30 N. Such latching ensures that it is not possible to accidentally change the needle position after the needle has been brought to the retracted position, and it is thus not possible to move the needle out of the safety mechanism.

Second latching elements are advantageously provided, which permit latching in the puncture position. Such latching in the puncture position facilitates the puncturing procedure, particularly if the force needed to release the latching is at least 5 N, preferably at least 8 N, particularly preferably $\geq 8$ to $\leq 13$ N, very particularly preferably $\geq 9$ to $\leq 11$ N.

The needle holder, which can serve at the same time as a grip, advantageously has a circumferential guiding and holding edge, which permits safe positioning, repositioning and release of the needle.

The port needle according to the invention preferably has a base, which is connected to the bearing and relative to which the needle can be brought into the at least two positions, namely the puncture position and the retracted position. Such a base affords the advantage of creating an easy-to-grip handle and/or a stable anchoring possibility for the further elements. It is entirely conceivable that the base and the bearing and other parts are produced all in one piece. The height compensation element can also be integrated in the base or form the latter.

A port needle according to the invention advantageously has an adhesion plate for securing the port needle or the bearing on the patient. This has the advantage that the port needle does not need to be bonded over after it has been applied, and instead it can be secured directly to the skin with the adhesion plate. Such an adhesion plate can be designed in very different ways. For example, it can be applied between bearing and patient or can be arranged all around the bearing. It can be prefabricated in a manner already connected to the height compensation element or can be supplied in an exact fit along with the port needle and affixed in place after the port needle has been applied. The adhesion plate is preferably made from a skin-friendly material with anti-allergenic adhesive material. In a preferred embodiment, the tissue material is transparent. Moreover, the adhesion plate can have an additional tab which, after the port needle has been applied, can be affixed over the needle to provide additional securing.

The port needle according to the invention is advantageously designed in such a way that the port needle has a lower height in the puncture position than in the retracted position. It is particularly advantageous if the height in the puncture position is less than the extent of the needle in the puncture direction. Puncture direction is to be understood as the direction in which the puncture takes place, that is to say generally perpendicular to the bearing surface. This is particularly advantageous since the port needle in some cases remains on the patient's skin for quite a long time. The port needle is then located in the puncture position. It is therefore expedient if the port needle in the puncture position has an especially low height. Height is to be understood here as the extent of the port needle lying between the bearing and the point farthest away from the bearing in the direction away from the patient. A low height thus increases the wearing comfort and reduces the risk of the port needle coming loose or being torn out.

On the other hand, the needle holder still has to be able to be gripped securely by the user. The port needle in the puncture position preferably has a height of $\geq 0.8$ cm and $\leq 1.8$ cm, particularly preferably of $\geq 1$ cm and $\leq 1.5$ cm.

An advantageous embodiment has at least two telescope segments, which are designed to be movable relative to each other and guided by each other. The needle is connected to one of the telescope segments, and another telescope segment is connected to the bearing. Connection of the needle to a telescope segment does not necessarily have to be done directly and instead can be effected via the needle holder. The same applies to the connection to the bearing, which connection can be established via the base, for example. In such a design of the telescope segments, the telescope segments are pushed as far as possible one inside the other in the puncture position and are pulled farther apart in the retracted position. Such a design as a telescope permits a very robust design with low overall height, which also has a high degree of stiffness in the retracted position. It is also possible for the needle in the retracted position to be enclosed completely by telescope segments, such that a breakage of the needle, which could cause further risks of injury, can be reliably avoided. The telescope segments are advantageously stacked inside one another in such a way that the innermost telescope segment is connected to the needle or to the needle holder. Such a connection can be effected, for example, by latching or adhesive bonding. However, the needle holder and innermost telescope segment can also be formed by the same element. It is particularly advantageous if the needle holder is in turn designed in such a way that it at least partially encloses all the telescope segments in the puncture position. In this way, in the puncture position, it is possible to achieve a particularly high degree of stability that favors the puncturing.

Advantageously, one telescope segment is connected to the base or forms the base and/or one of the telescope segments is connected to the needle holder or forms the needle holder. Such a design permits a very compact and robust design. When a height compensation element is used, it should be noted that the height compensation element is advantageously arranged between the bearing and the telescope segment arranged toward the bearing, in order to maintain the position of the needle relative to the telescope segments in a defined manner and to ensure an optimal effect of the height compensation element in the puncture position.

The needle holder is preferably latched by at least one releasable latching element, preferably at least two releasable latching elements, or also sliding or holding elements on the needle holder and on the fixed lower telescope segment. The latching is released by a pull exerted along the needle axis. The force needed to release the latching is influenced and determined by the latching angle of the latching elements, the width of the latching elements, the configuration of the geometry pairing, and also the flexibility and the material combination.

For controlled application of the port needle, it is of great importance that the safety mechanism is not triggered too early, such that even in the event of a position correction, which in extreme cases can even mean removal from the port membrane and reinsertion, the port needle can be handled safely and in a controlled way. For this purpose, it is preferable if the force needed to trigger the safety mechanism is 5 N or more, preferably at least 8 N. It is particularly preferable if a force of $\geq 8$ to $\leq 13$ N is needed, very particularly preferably a force of $\geq 9$ to $\leq 11$ N.

It is advantageous if the needle holder has closed, rounded surfaces for gripping.

The port needle advantageously has, on each telescope segment, at least one first latching element for the latching in the retracted position. These first latching elements can also be designed together with upper limits that protect against pulling out too far. The first latching elements, which prevent a pushing back, can be formed, for example, by latching tabs and/or latching lugs that engage with the lower edge or upper edge of the next element. It is advantageous if the latching elements are designed such that the safety mechanism withstands a pressure of at least 30 N, preferably a pressure of at least 40 N, in order to ensure that the safety mechanism cannot be released inadvertently.

In a preferred embodiment, the individual telescope elements are provided with a substantially circumferential inner stop rib, such that pulling of the segments is not possible at a pulling force of up to 30 N, preferably of up to 35 N.

The advantages of such latching have already been discussed in detail and are intended in particular to prevent the needle from being accidentally moved out from the retracted position.

A port needle according to the invention advantageously has, on each telescope segment, at least one first latching element for latching on to each adjacent telescope segment, in order in this way to reliably secure the latching in the retracted position. Middle telescope segments therefore have first latching elements for latching on to two other telescope segments. First latching elements can also be partly formed by or engage with edges and surfaces that are present anyway. The first and last or innermost and outermost telescope segments therefore only have first latching elements for latching on to another telescope segment.

The telescope segments stacked one inside the other preferably have such little play, and the telescope segment walls moving past each other are so shaped and so precise, that a twisting of the needle holder and/or jamming of the needle is prevented during the movement into the retracted position and/or in the retracted position.

In such a design, care should be taken to ensure that the stacked telescope segments are able to move telescopically in relation to one another without great resistance, but the play and in particular the orientation of the walls can be chosen such that an exclusively linear movement of the telescope segments is ensured. The telescope segments are preferably formed as hollow cuboids in which two opposite side faces extending perpendicular to the longitudinal extent of the needle are cut out. In this design, the telescope elements can move with particular precision in the linear direction. This linear direction of movement should extend perpendicular to the bearing surface. This assists the user in the exact retraction of the needle.

In a design of the telescope elements as round tube sections, further measures are advantageously taken to avoid twisting.

The needle is advantageously arranged inside the telescope segments. This means that, in the retracted position, the needle is completely enclosed laterally by telescope segments. However, if the needle is moved out of the retracted position, it is no longer arranged completely inside of telescope segments, but only inside of the telescope segments to the extent that it has not yet been moved axially out of these.

Four telescope segments are advantageously provided, of which the first one is connected to the base and the last one is connected to the needle holder. The use of four telescope segments has proven a particularly favorable compromise between stability and height of the port needle in the puncture position. It is particularly advantageous if the telescope segments used are in the form of hollow cuboids, in which two opposite side faces extending perpendicular to the longitudinal extent of the needle are cut out. By using hollow cuboids of this kind, particularly good stability against twisting and tilting can be achieved along with a low overall height.

Alternatively, tilting means can also be provided, which tilt the needle during the movement in the direction of the retracted position, such that the needle tip, after a certain predetermined movement in the direction of the retracted position, engages with the safety section and thus cannot be moved back out of the safety section in the direction of the puncture position. It is thus possible to ensure an effective protection against needle-prick injury even before the latching in the retracted position takes place or even without latching means. The tilting can, for example, have the effect that the needle tip is moved out of alignment with a hole in a cover plate and thus cannot be moved back through this hole in the direction of the puncture position. This can be achieved, for example, by inclined planes or an asymmetrical design of the individual telescope segments. Of course, such tilting is only effective if the needle tip is already located inside the safety section. In general, therefore, this (additional) protection mechanism is only relevant when no latching is provided or when the needle tip has already been brought into the safety section but the latching has not yet been effected. Thus, the tilting can also represent an additional protection mechanism in the event of failure of the latching in the retracted position. In any case, however, it provides protection in the event of operating errors in which no latching takes place.

The tilting means can advantageously be formed by differently designed first latching elements. For example, this can be achieved when, in the case of a multi-step latching of several telescope segments, the first latching also causes a tilting of the needle, for example by means of the latching tabs provided having a different length.

Advantageously, at least one first latching element for the latching in the retracted position, and for the latching of two telescope segments which preferably latch last during the movement into the retracted position, is designed in such a way that, upon latching, it produces a sound that differs from all the other sounds during the latching of the port needle. This means that the mutual latching of two telescope segments generates a sound that is characteristic of the port needle. When this characteristic sound is generated upon latching of the telescope segments latching last during the movement into the retracted position, this can be the signal to the user that a secure and lasting needle-prick protection has been achieved. Characteristic sounds of this kind can be obtained, for example, by a more solid design of latching tabs. The chosen telescope segments can be made to latch last by means, for example, of greater friction being provided between them than between the other telescope segments.

The telescope segment lying nearest to the bearing, that is to say lying nearest to the patient, advantageously forms the safety section. This means that the needle tip is located inside this telescope segment when the needle is in the retracted position. In addition, it is necessary for the needle tip to be drawn into this telescope segment to such a degree that, as a result of the interplay between the opening width of the telescope segment and/or an optional cover plate and the distance of the needle tip from this opening, it is possible to reliably avoid touching the needle tip.

Before use, the port needle is present in a form in which the needle protrudes far out of the needle holder, the telescope segments are stacked inside one another, and the safety mechanism is latched. In a preferred embodiment, the needle is provided with a protective sheath designed to prevent needle-prick injuries when preparing to apply the port needle. This protective sheath is preferably not clamped on the base plate but instead into one of the inner telescope segments, in order to ensure that, when the protective sheath is pulled, a pull is not exerted in the opposite direction on the grip element and base plate, which could lead to the safety mechanism being triggered.

The port needle according to the invention and the safety system can be provided and processed with antimicrobial additives.

This additive can be used in all individual plastic parts, but preferably in those parts that enclose the system. These are: grip piece (needle holder) and upper holding plate (fixed segment, component part of the leveling segment). Pathogens, which can colonize from the outside, find a surface that is hostile to their existence, and their growth is therefore decisively inhibited.

The above observations have made the invention clear and allow a person skilled in the art to make further embodiments adapted to the particular requirements. The illustrative embodiments that now follow serve merely to explain further advantages and possible modifications that may provide an additional or independent inventive contribution, even though not the subject matter of the attached claims, and are not in any way intended to limit the scope of protection. The drawings used for this purpose are purely diagrammatic and non-limiting.

BRIEF DESCRIPTION OF THE FIGURES IN THE DRAWINGS

FIGS. 1 to 13 show an embodiment with telescope segments 11 of hollow cuboid shape. Such a design offers a high degree of stability with minimal overall height, both in the puncture position and also in the retracted position and all intermediate positions. It is also particularly secure against twisting and, with precise matching of the telescope segments 11, permits good guiding of the needle.

Figure 1:
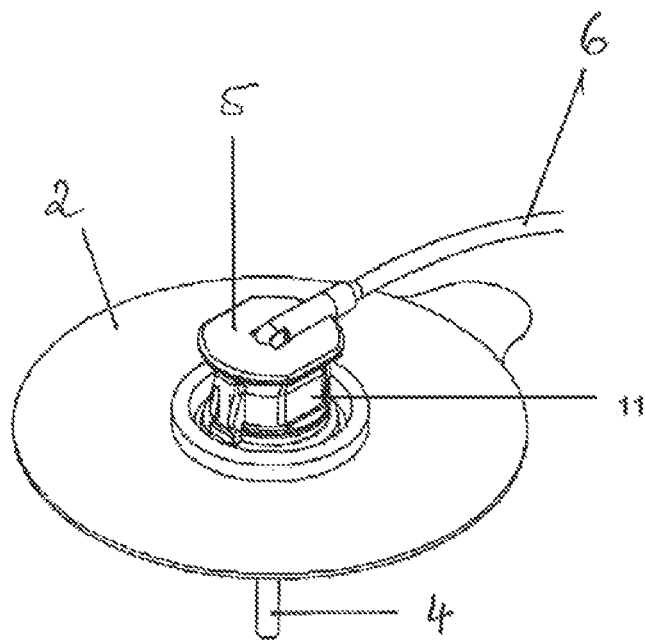
FIG. 1 shows a perspective view of a with telescope segments.

FIG. 1 shows a view of a port needle in the puncture position, with the needle guard 4 present in the state as supplied. The figure also shows the hose 6, the adhesion plate 2, and the needle holder 5 in which an end of the needle is secured, wherein there is a connection between needle and hose 6. Under the adhesion plate 2, which is formed by a plaster, there is a bearing connected to the base.

Figure 2:
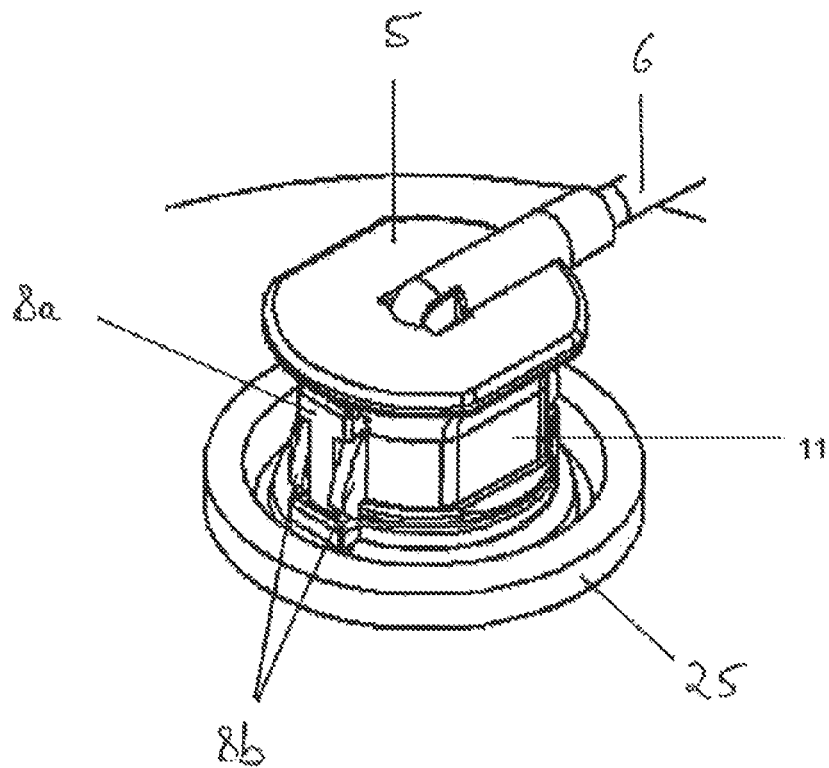
FIG. 2 shows a detail of the view in FIG. 1.

FIG. 2 shows the latching of the safety mechanism in the puncture position. In this position, the needle holder 5 is latched onto the first telescope element 11. The mechanism, releasable by pulling, consists of a movable clip tab 8a and a pair of slide ribs 8b, the mechanism shown being located on two sides of the needle holder 5.

Figure 3:
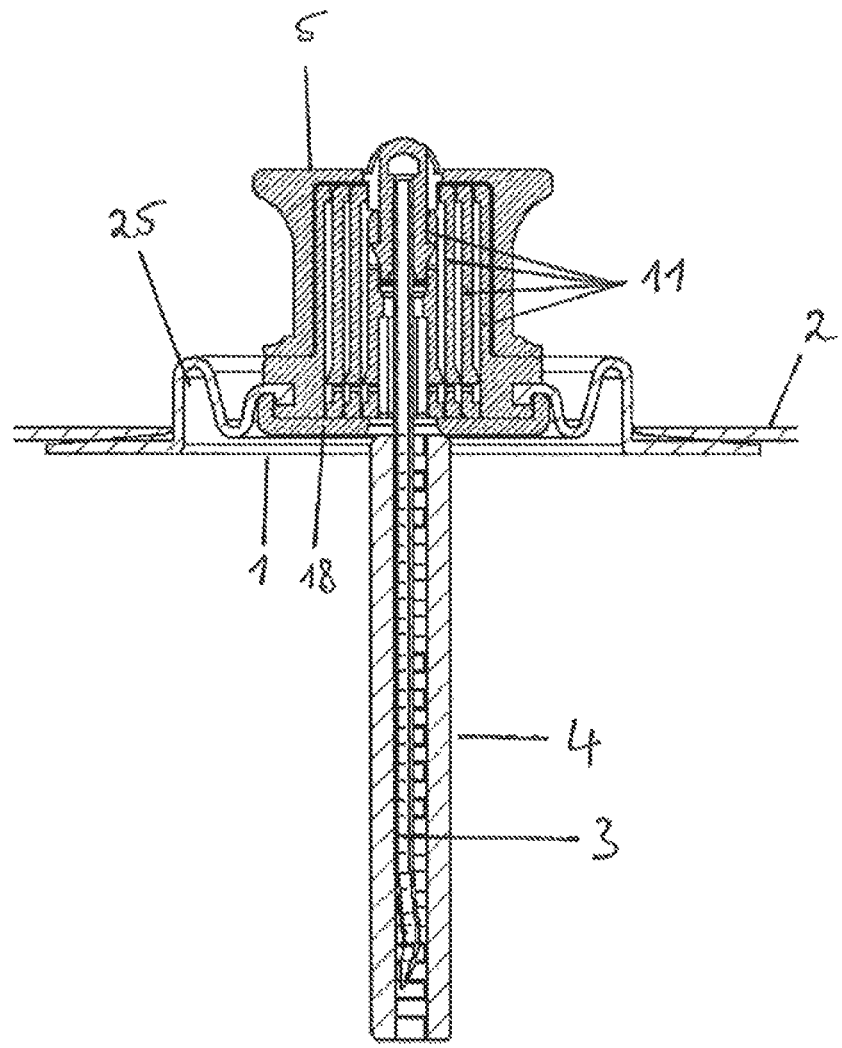
FIG. 3 shows a cross-sectional view of a port needle in the puncture position.

FIG. 3 shows a cross-sectional view of the view from FIG. 1. In addition to the needle 3, the figure shows the bearing 1 and the adhesion plate 2. The bearing 1 is designed in one piece with the height compensation element 25 and the base 18. The bearing 1 is located under the circumferential adhesion plate 2. The figure also shows telescope segments 11. In the example shown here, four telescope segments 11 are provided. The first telescope segment 11 is connected to the height compensation element 25, and the fourth and innermost telescope segment 11, which has the smallest diameter, is connected to the needle holder 5. In the puncture position, the telescope segments 11 are all driven inside one another, such that the port needle has a low height of approximately 1.5 cm between the bearing 1 and the uppermost point of the needle holder 5. This is particularly advantageous since, during the puncturing, only a relatively small but nevertheless easily grippable and inherently stable part has to be maneuvered by the user. In addition, the port needle may possibly remain for quite a long time on the patient, with a substantial part of the port needle being arranged on the surface of the patient's skin. A low height therefore promotes the wearing comfort and additionally prevents accidental tearing out or loosening of the port needle.

Figure 4:
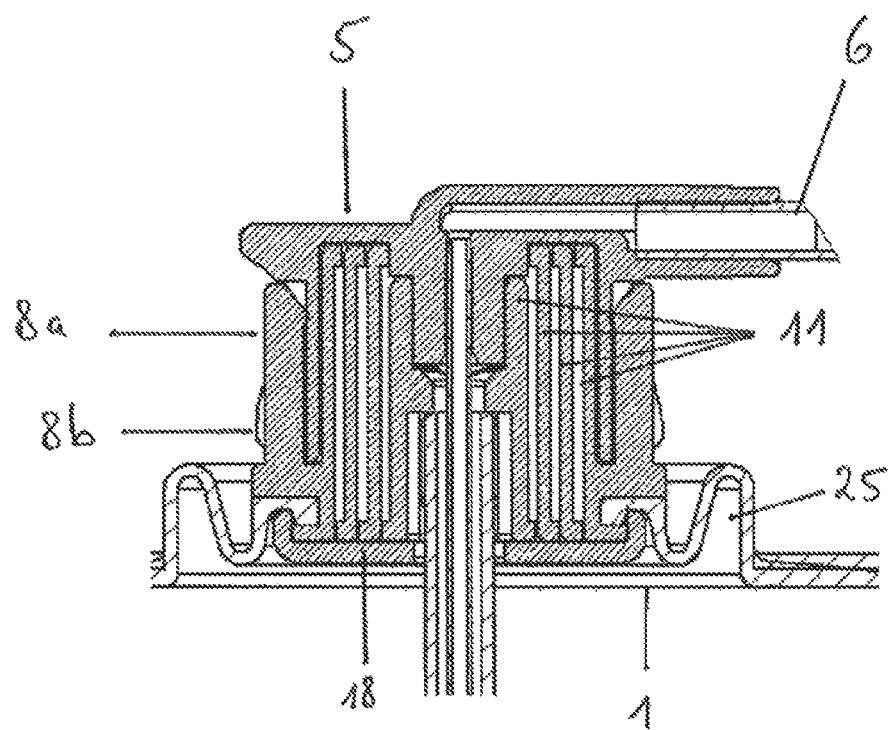
FIG. 4 shows a cross-sectional view, turned in relation to FIG. 3, of a port needle in the puncture position.

FIG. 4 likewise shows a cross-sectional view of a port needle in a design according to the view in FIG. 1, but with the section plane turned through 90° in relation to FIG. 3. The figure shows the needle 3 secured in the needle holder 5. The hose 6 is connected to the needle holder. This figure again shows the four telescope segments 11, of which the outermost and first is connected to the base 18 and to the bearing 1 via the height compensation element 25. The innermost, fourth and therefore last telescope segment 11 is connected to the needle holder 5. The needle holder 5 has the slide ribs 8b, which engage with the clip tabs 8a on the lowermost telescope element. These elements 8a and 8b permit latching in the puncture position. Second latching elements 17 are arranged on the telescope segments 11 and also on the needle holder 5. If the needle holder is pulled with a force of approximately 9-12 N, with simultaneous fixing of the base by pressure on the adhesion plate or on the height compensation plate, the safety mechanism is triggered.

Figure 5:
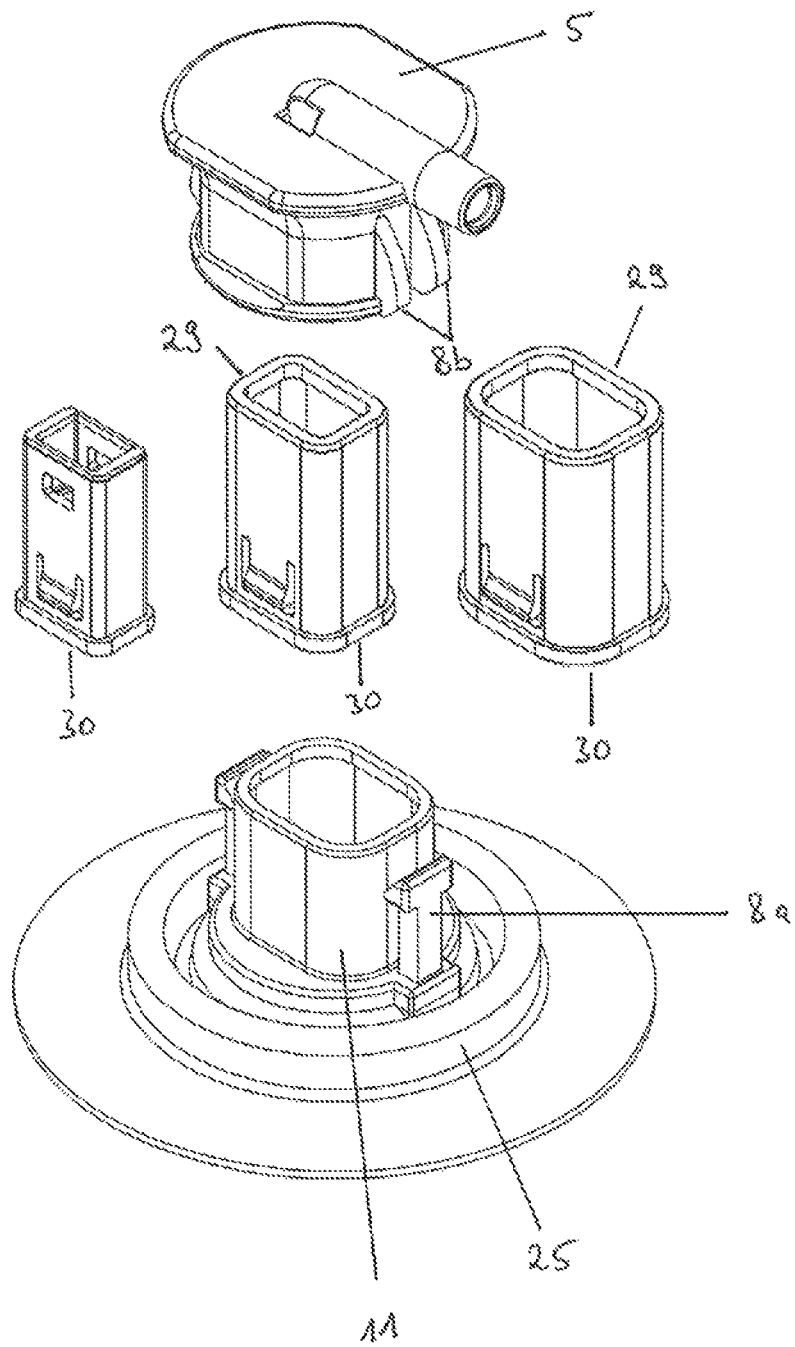
FIG. 5 shows a detailed view of the elements of the telescope structure.

FIG. 5 shows the needle holder 5, three telescope elements 11, and the lower telescope element 11, which is connected to the height compensation plate. The slide ribs 8b are located on the needle holder, and the clip tabs 8a on the lower telescope element 11. The latching elements 17 can also be seen on the other telescope elements 11.

The telescope segments 11 additionally have upper limits 29. These upper limits 29 are arranged at the upper end of the first three telescope segments 11 and engage with lower abutments 30 mounted on the lower end of each of the last three of the telescope segments 11. By means of their engagement, the upper limits 29 and lower abutments 30 prevent the telescope segments from being drawn too far apart or being released.

Figure 6:
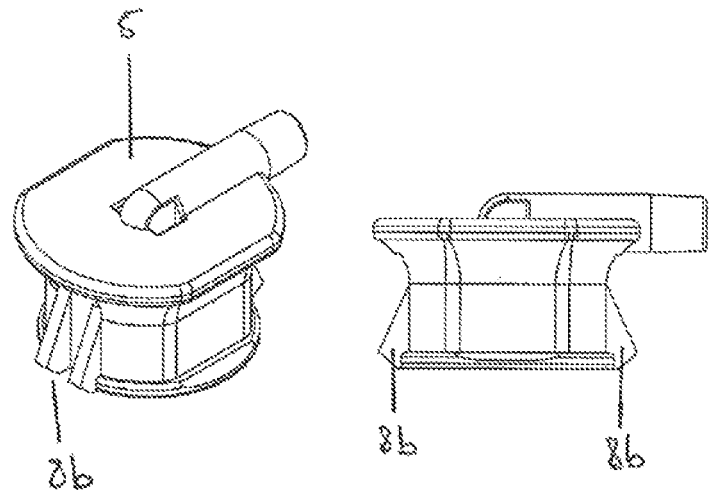
FIGS. 6, 7, 8 show different embodiments of the slide ribs 8b.
Figure 7:
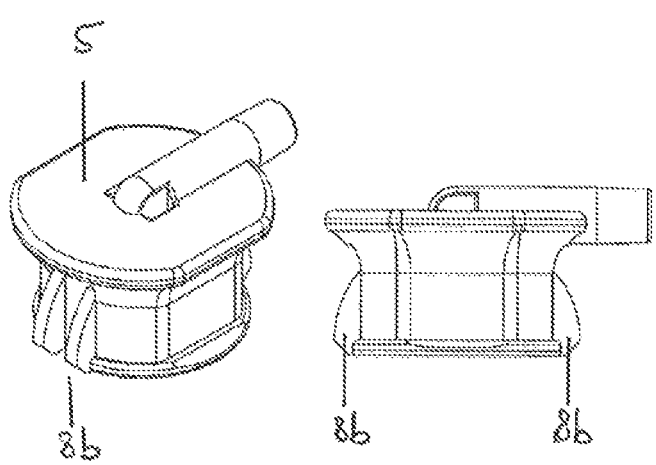
Figure 8:
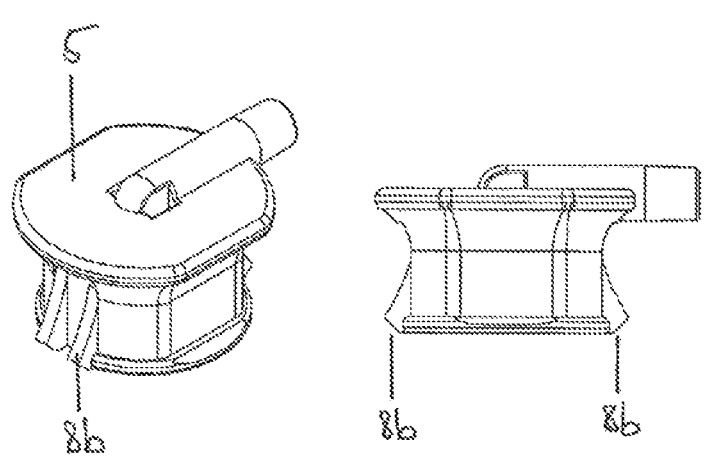

FIGS. 6, 7 and 8 show different geometries of the slide ribs. In FIG. 6, the ribs are straight. This means that the force profile for releasing the safety mechanism is linear. In FIG. 7, by contrast, the shape of the slide rib is convex. Such a shape of a slide rib requires a high initial force to trigger the safety mechanism. FIG. 8 shows an embodiment with a concave force profile, i.e. a low initial force is required, but a high force needs to be applied for the final unlocking.

Figure 9:
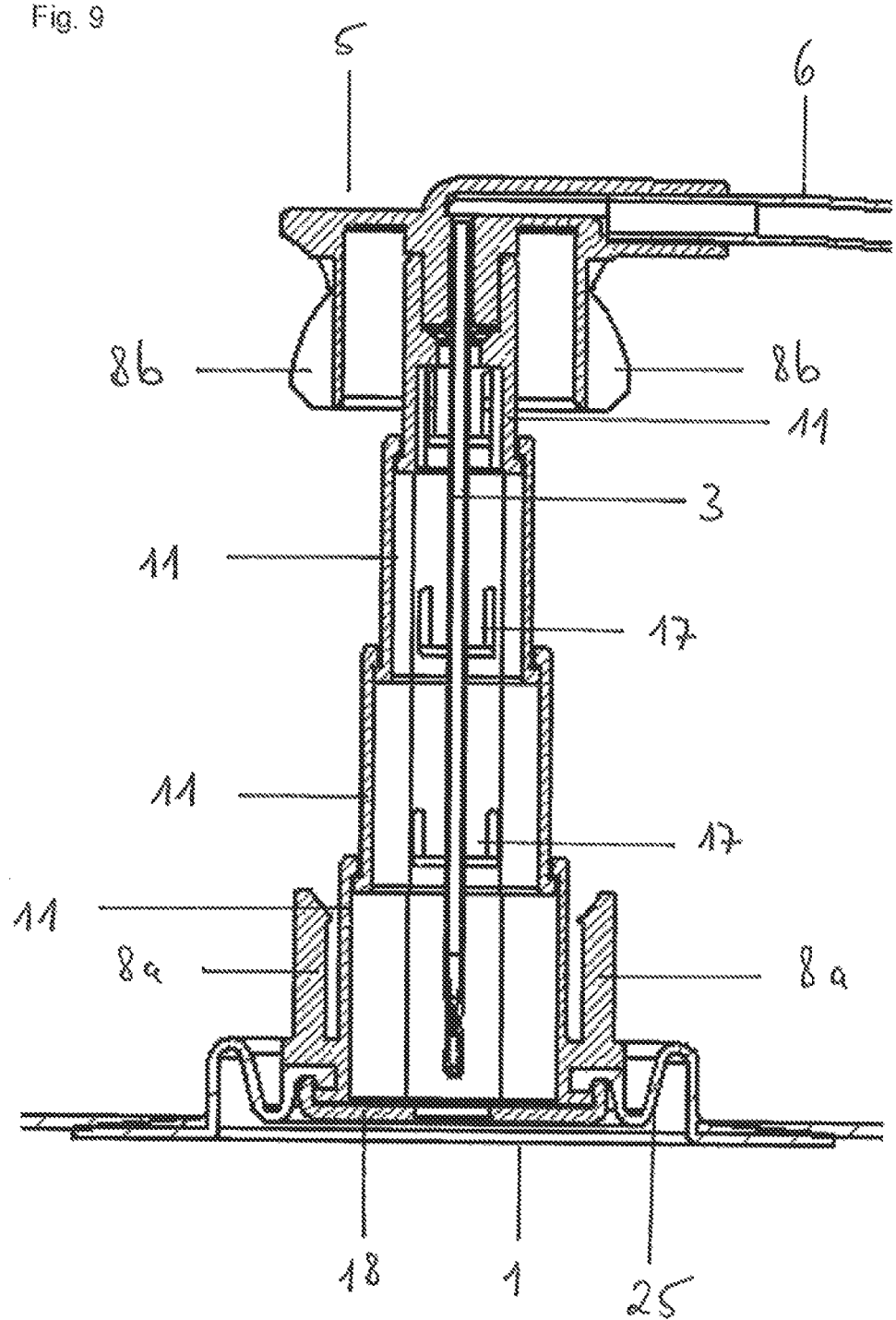
FIG. 9 shows a cross-sectional view of a port needle with telescope elements and drawn-out safety mechanism.

FIG. 9 shows a cross section through a port needle with the safety mechanism drawn out and latched. The needle holder 5 is connected to the needle 3 and to the hose 6 and has, in the upper area, a holding rib. The slide ribs 8b are located on the needle holder 5. The upper telescope element 11 is connected to the needle holder 5 by a non-releasable clip connection. The telescope elements 11 are latched together by latching elements 17. The lower telescope element 11 is connected to the height compensation plate and has clip tabs 8a, which engage with the slide ribs 8b.

Figure 10:
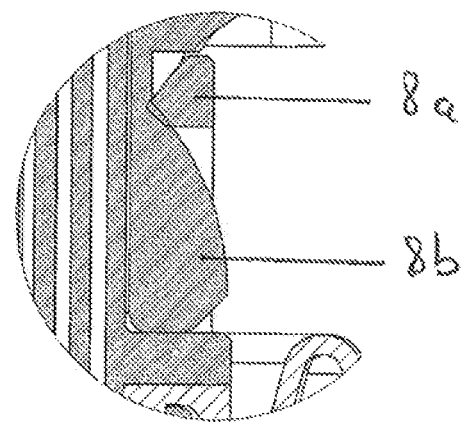
FIG. 10 shows a detail of an embodiment of the latching mechanism 8.

FIG. 10 shows in detail the engagement of clip tab 8a and slide rib 8b.

Figure 11:
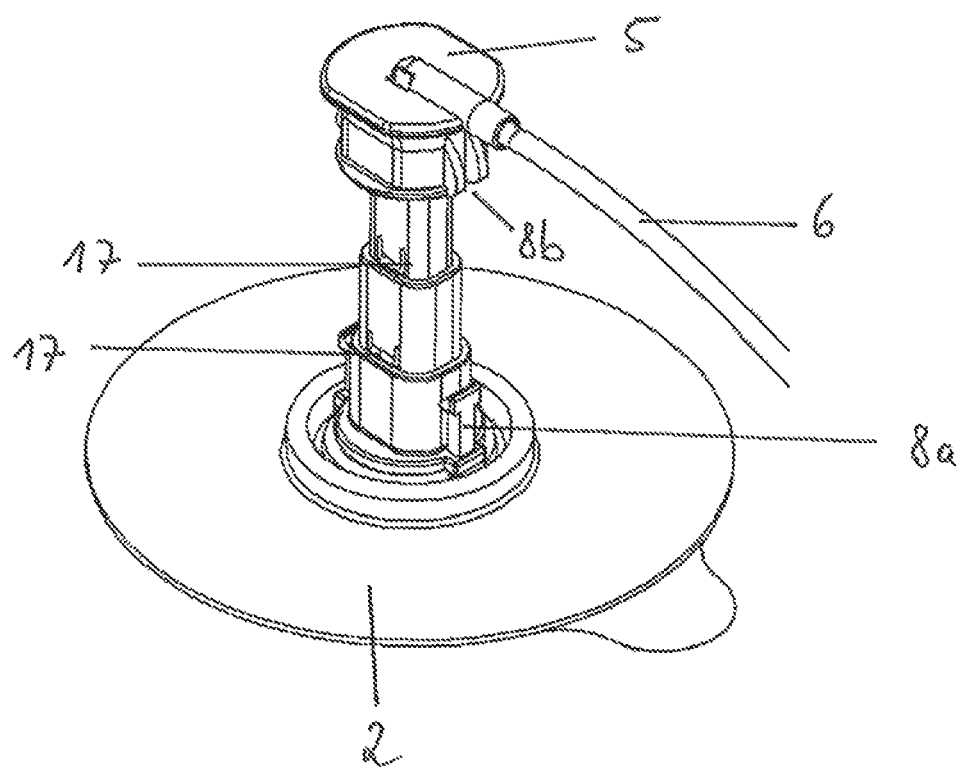
FIG. 11 shows a perspective view of a port needle with telescope elements and drawn-out safety mechanism.

FIG. 11 shows a view of the port needle with the safety mechanism drawn out. The latching elements are designed as clip lugs and clip tabs.

Figure 12:
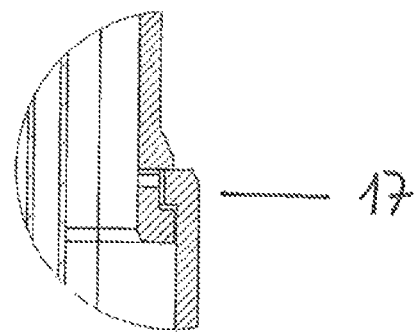
FIG. 12 shows a detail of an embodiment of the latching mechanism 17.

FIG. 12 shows a detail of the latching from FIG. 11.

Figure 13:
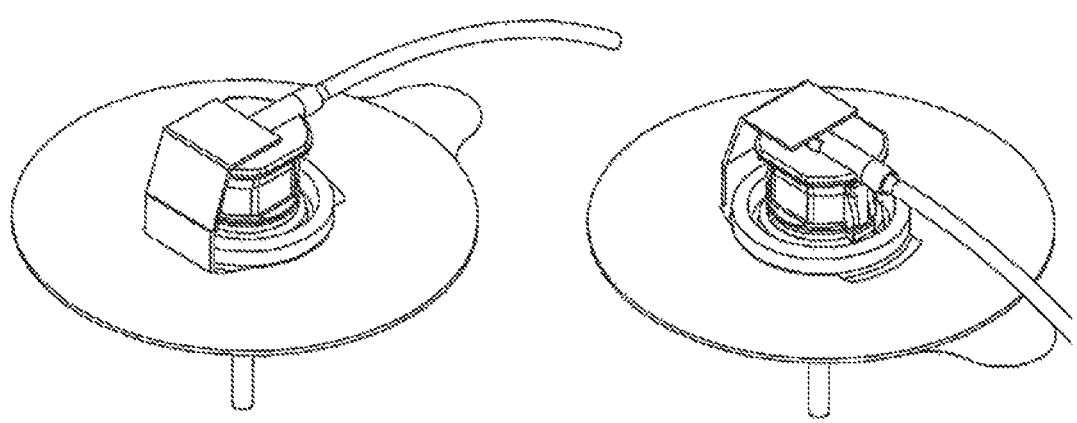
FIG. 13 shows an alternative design of the plaster.

FIG. 13 shows an embodiment in which the plaster has an additional tab that can be affixed over the port needle after the latter has been applied. This additional fixing is a further mechanism for protecting against accidental detachment.

The embodiments described in the examples were tested in a comparison with safety port needles available on the market. The aim of this measurement was to determine the force needed to trigger the safety mechanism.

Measurement equipment: Erichsen Physimeter 906 MCB—200 N.

The examples according to the invention (different embodiments) required a force of 9-11 N to trigger the safety mechanism.

BBraun Surecan SafeStep: extraction force (releasing the safety mechanism) 1.2 N.

PFM EZ Huber Safety Infusion Set: extraction force (releasing the safety mechanism) 1.75 N.

The comparison with two typical products on the market revealed that the force needed to trigger the safety mechanism in the examples according to the invention is greater by at least a factor of 5.

An example according to the invention, with telescope drawn out and latched, withstood a pressure of up to 63 N along the needle axis.

Values determined by means of pressure test with the TesT Universal testing machine 106.2 KN.H.

A design according to the invention with a circumferential stop rib in the telescope elements withstood a pulling force of up to 40 N without the elements being able to be drawn apart from one another in the drawn out form.

Values determined by means of tension test with the TesT Universal testing machine 106.2 KN.H.

Figure 14:
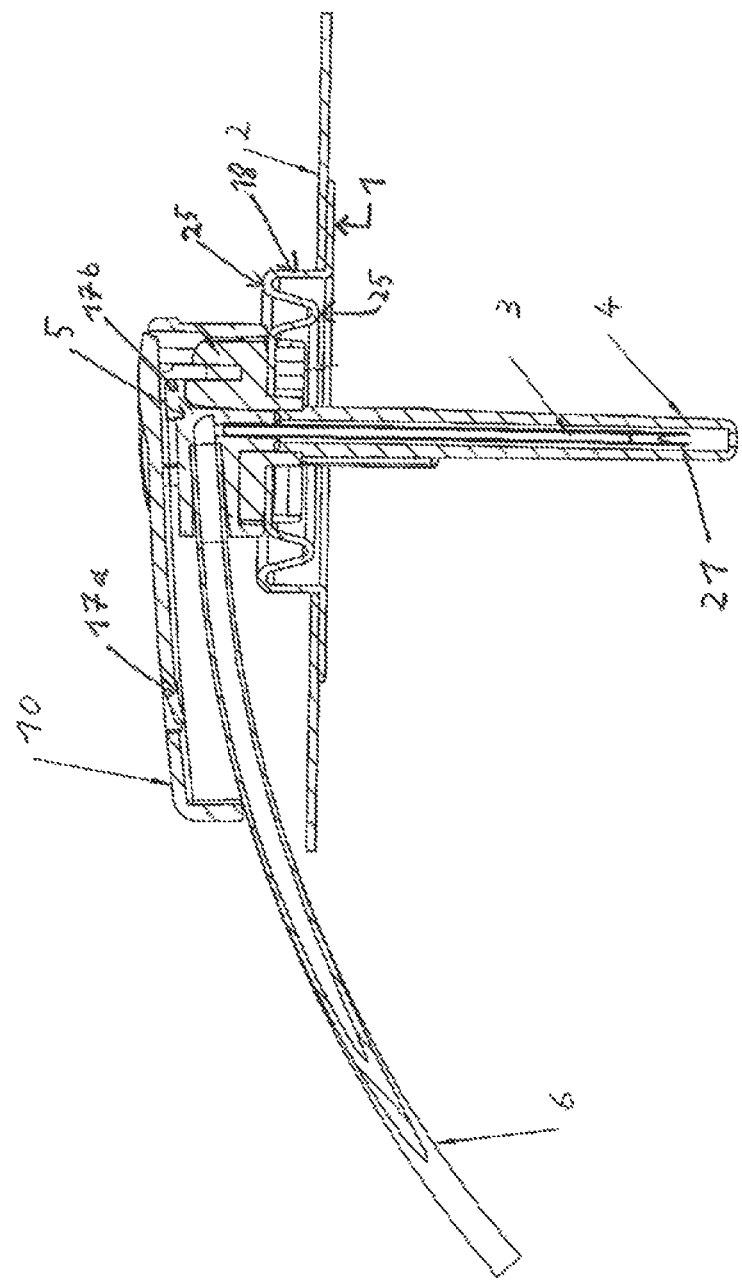
FIG. 14 shows a cross-sectional view of an embodiment of a port needle with needle-prick protector in the puncture position, where the safety mechanism is activated by releasing a lever.

FIG. 14 shows a cross-sectional view of such a port needle with the lever 10 in the puncture position. The figure shows the bearing 1, which is surrounded by an adhesion plate 2, the base 18, which contains a height compensation element 25, the needle 3 with the needle tip 21, which is surrounded by a needle guard 4, the lever 10, the needle holder 5, a hose 6, and first latching elements 17a, 17b for the latching in the retracted position. The needle 3 is connected to the hose 6. This connection lies inside the needle holder 5, on which the needle 3 and the hose 6 are secured. The needle holder 5 is connected to the base 18 via a U-shaped profile, which extends farther over the lever 10. The bearing 1 is connected to the base 18 and to the adhesion plate 2. The height compensation element 25, which serves to compensate for the puncture depth, is integrated in the base 18 by means of the undulating configuration.

For use, the needle guard 4 is first of all removed, and a puncture is then made with the needle 3 or needle tip 21. At the end of this procedure, the port needle comes to lie with the bearing 1 on the patient or on the port. The port needle is then secured on the patient with the adhesion plate 2. A substance can now be introduced into the port via the connection existing between hose 6 and needle 3. The height compensation element 25 can compensate for relative movements between needle 3 and bearing 1 and for deviations between the length of the needle 3 and the depth of the port base.

Figure 15:
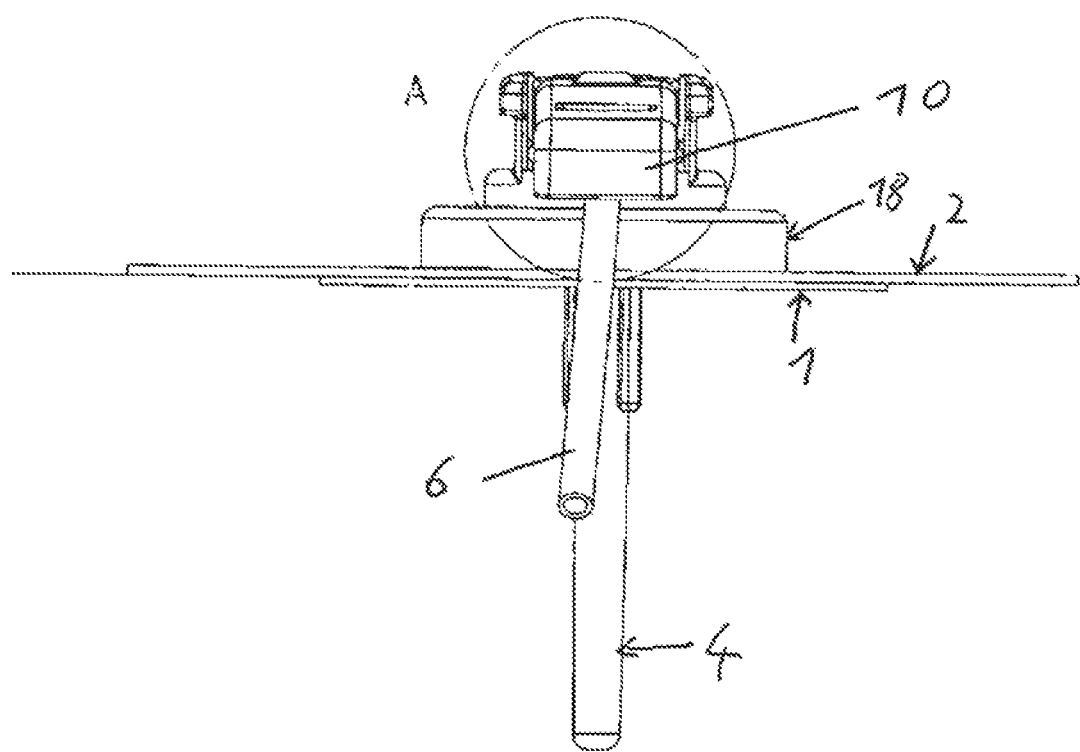
FIG. 15 shows a rear view of a port needle according to FIG. 14.
Figure 16:
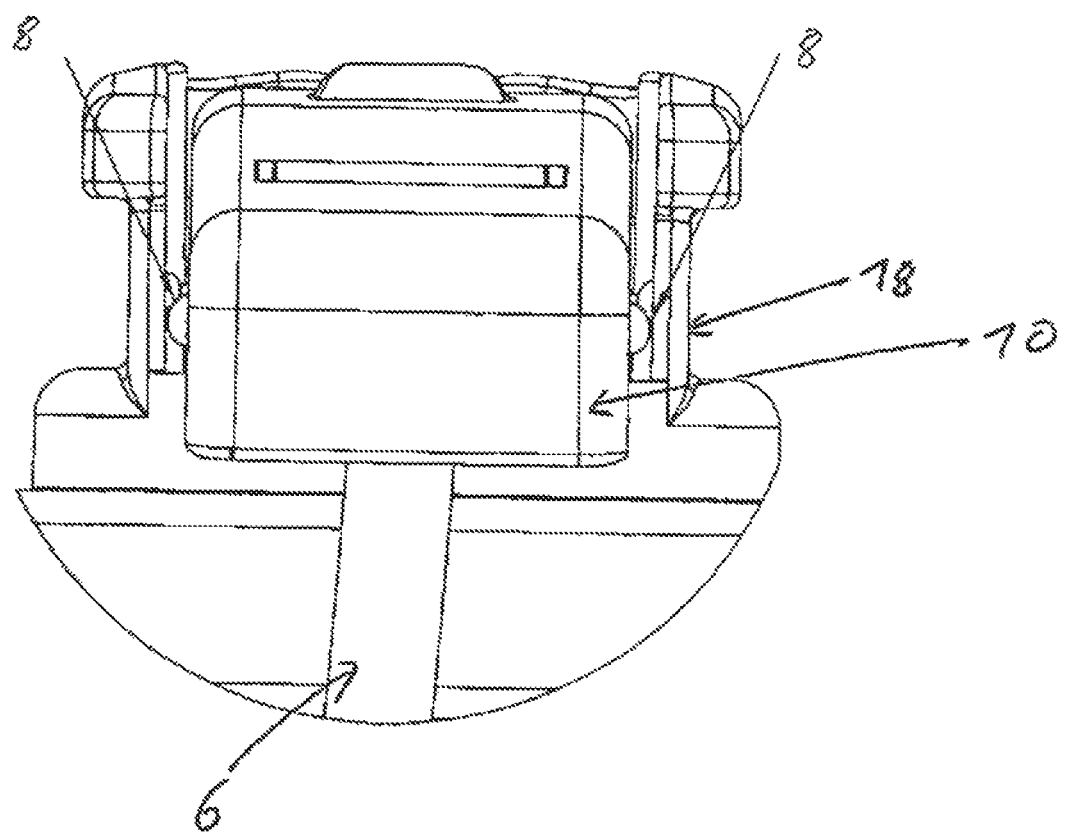
FIG. 16 shows a detail from FIG. 15.

FIG. 15 once again shows the port needle in a rear view, in the state as supplied with needle guard 4. The detail indicated in FIG. 15 by a circle and by reference sign "A" is reproduced on a larger scale in FIG. 16. FIG. 16 thus shows a rear view of a detail of the port needle. It shows the hose 6 and the lever 10, and also the base 18. Second latching elements 8 for the latching in the puncture position are mounted respectively on the base 18 and on the lever 10. These second latching elements 8 secure the puncture position and permit reliable puncturing, without the needle 3 being able to move appreciably in relation to the other elements of the port needle, particularly the bearing 1 and the base 18. Quite small movements, which are permitted by the height compensation element 25, do not adversely affect the puncture.

Figure 17:
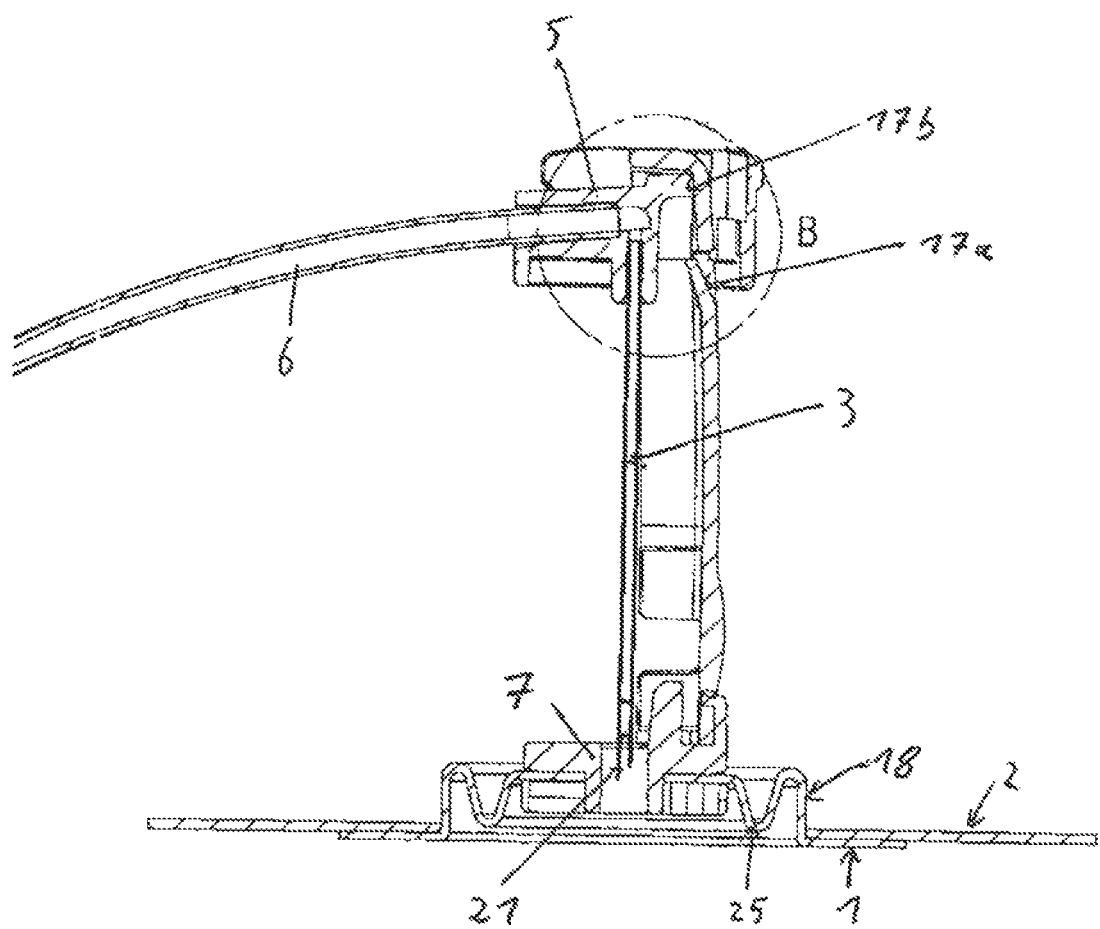
FIG. 17 shows a port needle with lever in the retracted position.

FIG. 17 shows the state of the port needle in the retracted position. To reach this position, starting from the view in FIG. 14, the lever 10 is first of all pivoted upward through 90°. The needle 3 with the needle holder 5 and the hose 6, supported by the guide provided by the U-shaped profile on the needle holder 5 and the lever 10, is then pulled upward along the lever 10. In this way, the needle 3 is withdrawn from the port or from the patient. This state is shown in FIG. 17. The latter shows the retracted needle 3, with the needle tip 21 arranged in the safety section 7. It is clear from this view that the needle tip 21 is enclosed by the safety section 7 in such a way that it is not possible to accidentally touch the needle tip 21. Although the needle 3 is not completely surrounded, it is nevertheless sufficiently enclosed from the side, in particular at the needle tip 21, to ensure that contact with the needle tip 21 can be reliably avoided. The first latching elements, provided for the latching in the retracted position and designed as latching lug 17b on the needle holder 5 and as latching tab 17a on the lever 10, prevent a movement of the needle tip 21 out of the safety section 7. However, the first latching elements 17a, 17b do not prevent all movement of the needle 3 or of the needle holder 5 or needle tip 21. Instead, they allow a certain play, such that a movement in the direction of the retracted position is also permitted beyond the point of latching. This improves the safety of use by increasing the likelihood of reliable latching by the user.

Figure 18:
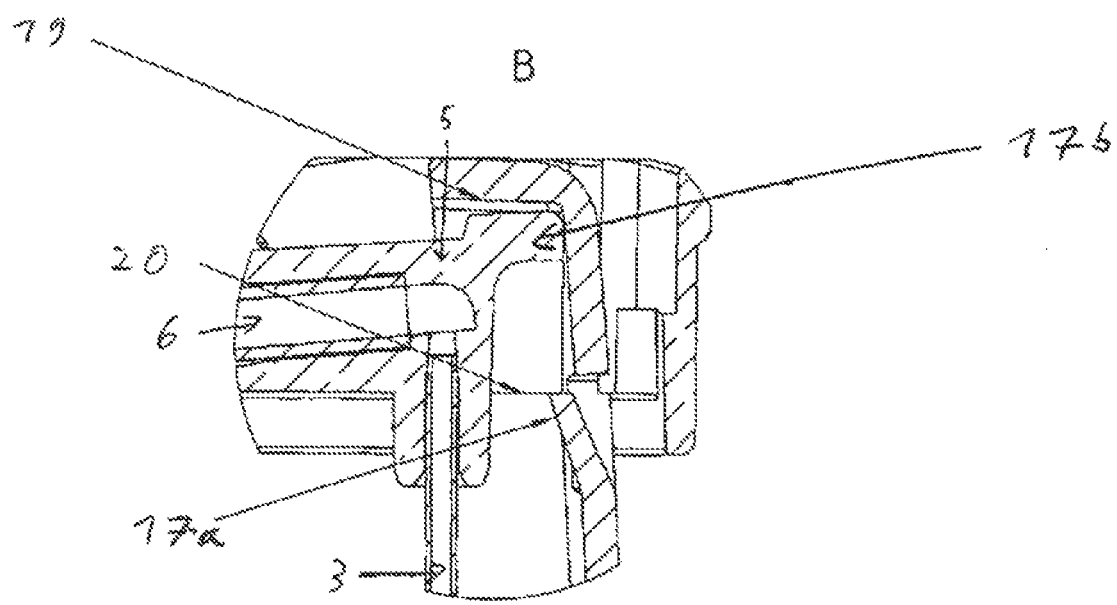
FIG. 18 shows a detail from FIG. 17.

The area indicated in FIG. 17 by a circle and by reference sign "B" is shown on a larger scale in FIG. 18.

FIG. 18 thus shows a detail from FIG. 17 and shows the end area of the lever 10 with the needle holder 5. It once again clearly shows that the needle holder 5 has, as first latching element for the latching in the retracted position, a latching lug 17b which engages with the latching tab 17a provided as further first latching element on the lever 10 for the latching in the retracted position, in such a way that a movement of the needle 3 in the direction of the puncture position is prevented with a certain play. This play between the upper limit 19 and the lower limit 20 can be clearly seen in FIG. 18, since the needle holder 5 has been pulled up as far as the upper abutment on the upper limit 19. From there, it has only a certain play in the downward direction until the latching lug 17b, as one of the first latching elements for the latching in the retracted position, on the needle holder 5 is brought into engagement with the latching tab 17a, for the latching in the retracted position, on the lever 10 at the lower limit 20. Such play is not harmful, however, and is even beneficial for secure latching in the retracted position, since the user in such a case is able to move the latching lug 17b easily and safely past the latching tab 17a provided on the lever 10 for the latching in the retracted position.

The safety section 7 is accordingly of such a size that, even when the existing play is utilized, there is no danger of the needle tip 21 being touched.

The invention claimed is:

1. A port needle having
    a bearing for resting the port needle on the patient,
    a first latching element connected to the bearing, the first latching element including a plurality of flexible clips,
    a needle holder including a plurality of ribs,
    a feed line secured on the needle holder,
    a needle secured on the needle holder and including a tip, the needle being positionable into a puncture position and a retracted position, wherein the one or more ribs of the needle holder engage the one or more flexible clip members of the first latching element to form a releasable connection between the bearing and the needle holder when the needle is in the puncture position, and
    a safety section, which shields the tip of the needle at least in the retracted position and thus forms a needle-prick protection device.

2. The port needle as claimed in claim 1, wherein the port needle has a flexible and/or extensible height compensation element positioned between bearing and needle.

3. The port needle as claimed in claim 1, further comprising a second latching element configured to latch the needle in the retracted position.

4. The port needle as claimed in claim 1, wherein the first latching element is secured during the puncture.

5. The port needle as claimed in claim 1, wherein the needle, in order to be brought into the at least two positions, can be moved relative to a base, which is rigidly connected to the bearing.

6. The port needle as claimed in claim 1, wherein it has an adhesion plate for securing the bearing on the patient.

7. The port needle as claimed in claim 1, wherein it has at least two telescope segments, which are designed to be movable relative to each other and guided by each other, wherein the needle is connected to one of the telescope segments, and another telescope segment is connected to the bearing, and wherein the telescope segments are nested one inside the other in the puncture position and are pulled apart in the retracted position.

8. The port needle as claimed in claim 7, wherein one of the telescope segments is connected to a base or forms the base and/or one of the telescope segments is connected to the needle holder or forms the latter.

9. The port needle as claimed in claim 7, wherein each telescope segment has a second latching element for the latching in the retracted position.

10. The port needle as claimed in claim 9, wherein the telescope elements are stacked one inside the other and can be latched onto each adjacent telescope segment using the second latching element.

11. The port needle as claimed in claim 10, wherein the telescope segments stacked one inside the other each have such little play, and a precise configuration and shaping of the walls moving past each other, that a twisting of the needle holder and/or jamming of the needle is prevented during the movement into the retracted position and/or in the retracted position.

12. The port needle as claimed in claim 7, wherein the needle is arranged inside the telescope segments.

13. The port needle as claimed in claim 7, wherein four telescope segments are provided, which are formed in particular from hollow cuboids with in each case two cut-out side faces.

14. The port needle as claimed in claim 7, wherein the telescope segment lying nearest to the bearing forms the safety section.

15. The port needle of claim 1 wherein the one or more flexible clips are configured to flex to move over a surface of the one or more ribs as the needle is moved between the puncture position and the retracted position.

16. The port needle of claim 15 wherein the surface of the one or more ribs is a curved surface.

17. The port needle of claim 1 wherein the needle holder and the first latching element are configured such that the force needed to release the connection between the needle holder and the first latching element is at least 5 N.

* * * * *